United States Patent [19]

Køhnke

[11] 4,257,453

[45] Mar. 24, 1981

[54] PEEP VALVE WITH IMPROVED VIBRATION DAMPING

[75] Inventor: Ole B. Køhnke, Lyngby, Denmark

[73] Assignee: Ruth L. Hesse, Rungsted Kyst, Denmark

[21] Appl. No.: 11,672

[22] Filed: Apr. 6, 1979

[51] Int. Cl.³ .................... F16K 15/02; F16K 47/00
[52] U.S. Cl. ................................................. 137/514.3
[58] Field of Search ............... 137/514, 514.3, 514.5, 137/514.7, DIG. 9

[56] References Cited

U.S. PATENT DOCUMENTS

| | | | |
|---|---|---|---|
| 696,074 | 3/1902 | Osmel | 137/514.5 X |
| 1,036,387 | 8/1912 | Wainwright | 137/514.3 |
| 2,002,451 | 5/1935 | Gray | 137/514.5 |
| 2,299,079 | 10/1942 | Davis | 137/514.3 X |
| 2,530,536 | 11/1950 | Oldham et al. | 137/DIG. 9 |
| 3,850,405 | 11/1974 | White | 137/514.3 X |
| 4,182,366 | 1/1980 | Boehringer | 137/514 |

*Primary Examiner*—William R. Cline
*Attorney, Agent, or Firm*—Spencer & Kaye

[57] ABSTRACT

An expiration valve composed of a valve housing presenting an inlet arranged to be connected to the expiratory outlet of ventilating apparatus, and an outlet, a valve seat disposed within the housing, a valve disc arranged to cooperate in a sealing manner with the valve seat, a member biasing the valve disc into its sealing position against the valve seat in the direction counter to the air flow direction between the inlet and the outlet, and a damping chamber containing a viscous fluid and arranged to cause movement of the viscous fluid within the chamber to damp vibrations of the disc during movement of the disc within the housing.

5 Claims, 1 Drawing Figure

U.S. Patent    Mar. 24, 1981    4,257,453
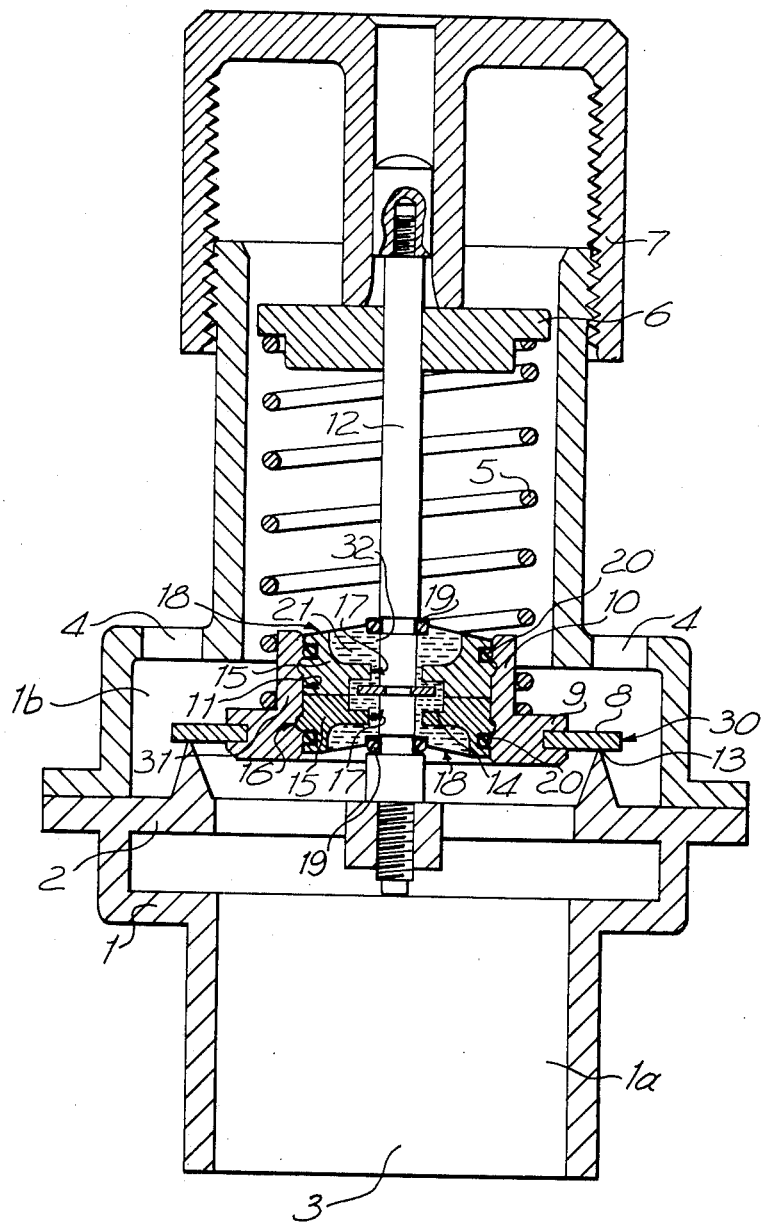

PEEP VALVE WITH IMPROVED VIBRATION DAMPING

BACKGROUND OF THE INVENTION

The present invention relates to an expiration valve of the type intended to be connected to the expiratory outlet of apparatus for artificial positive pressure ventilation of a patient's lungs, in order to create a positive pressure which is retained in the patient's lungs when expiration, or exhalation, has terminated.

This form of artificial ventilation of a patient's lungs, where the patient exhales to a controlled positive pressure level and not to the atmospheric pressure, is known as "PEEP" ventilation, PEEP being an acronym for Positive End-Expiratory Pressure ventilation.

Various kinds of PEEP valves that permit such ventilation to be carried out are known in the art.

The simplest kind of PEEP valve consists of a flexible tube one end of which is attached to the expiratory outlet of the apparatus and the other end of which is immersed in water or other fluid, so that air expired by a patient has to displace the water column present in the tube in order to escape and rise to the surface of the water in the form of bubbles. The end-expiratory pressure thus becomes equal to the depth to which the tube is immersed in the water. Such an arrangement is, however, only suitable for use in conditions in which a receptacle for the fluid can be firmly supported and kept steady.

Other arrangements are known in which the expiratory outlet of ventilating apparatus is connected to a valve opening leading to a valve seat covered by a diaphragm, the downstream side of which is loaded by an adjustable pneumatic pressure, so that expiration via the valve can only occur as long as the expiratory pressure is capable of lifting the diaphragm free of the valve seat against the downstream pneumatic pressure.

Such valve arrangements can, however, only be used in circumstances in which an accurately controllable and adjustable course of pneumatic pressure is available for loading the diaphragm, e.g. from the control system of a respirator.

Furthermore, spring-loaded PEEP valves are known, such valves being composed of an inlet adapted for connection to the expiratory outlet of ventilation apparatus and leading to a valve seat which is covered on its downstream side by a spring-loaded valve disc, so that expiration only takes place via such a valve if the expiratory pressure is capable of opening the valve against the spring force acting on the valve disc.

Spring-loaded PEEP valves have the advantage of being compact and usable without requiring pneumatic pressure or a fluid receptacle. However, known designs have had the disadvantage that they tend to vibrate during expiration, reducing the accuracy of the valve's setting capability and producing an unacceptably high noise level.

SUMMARY OF THE INVENTION

It is an object of the present invention to prevent, or at least reduce, the occurrence of undesirable vibrations associated with expiration valves.

This and other objects are achieved, according to the present invention, by the provision of an expiration valve composed of a valve housing presenting an inlet arranged to be connected to the expiratory outlet of ventilating apparatus, and an outlet; a valve seat disposed within the housing; a valve disc arranged to cooperate in a sealing manner with the valve seat; means biasing the valve disc into its sealing position against the valve seat in the direction counter to the air flow direction between the inlet and the outlet; and means defining a damping chamber containing a viscous fluid, for causing movement of the viscous fluid within the chamber to damp vibrations of the disc during movement of the disc within said housing.

BRIEF DESCRIPTION OF THE DRAWING

The sole FIGURE is a longitudinal cross-sectional view of a preferred embodiment of an expiration valve according to the invention.

DESCRIPTION OF THE PREFERRED EMBODIMENTS

The illustrated expiration valve consists of a two-part, substantially circular cylindrical valve housing 1 that is divided into two chambers by means of an annular partition 2. A first, inlet, chamber 1a includes an opening 3 adapted for airtight connection to the expiratory outlet of an apparatus for artificial positive pressure ventilation of a patient's lungs, and a second, outlet, chamber 1b communicates with the atmosphere via openings 4 in the wall of the valve housing 1.

The inner edge of the partition 2 is formed to provide a circular, knife-edged valve seat 13 disposed on the downstream side of partition 2 and engaged by a valve disc 30 that is urged against seat 13 by the action of a coil spring 5 disposed within chamber 1b. The spring 5 is so placed that one end of the spring rests on the valve disc 30 and the other end seats on a mobile means 6 in the form of a disc that is adjustably retained in position by a threaded cap 7 that is screwed onto an end portion of housing 1 and is thus movable in the direction of the longitudinal axis of spring 5 so that the spring force acting on the valve disc 30 can be adjusted by rotating threaded cap 7.

The valve disc 30 is composed of a circular, highly flexible annular diaphragm ring 8 of rubber or similar elastic material that forms the circumference of the valve disc and that is capable of completely sealing the opening in the partition 2 in response to even light pressure on the downstream side. An outwardly extending flange 9 of a support member 31 made of lightweight, rigid material, e.g. a suitable plastic material, is secured to the internal circumference of ring 8. The support member 31 further includes a central hub portion 10 that extends axially in the interior of the compressively pre-stressed spring 5, at the end thereof which seats on the downstream side of the flange 9. The hub portion 10 has an internal bore 11 that extends centrally and axially throughout the support member 31.

A valve rod 12 is fixedly secured within the valve housing, so as to be aligned with the longitudinal axis of the housing and extend through bore 11, and thus extends at right angles to the disc seat 13. A small disc 14 is fixed to the rod 12 at a location within bore 11 and is arranged to limit the axial movement of valve disc 30 in relation to the rod 12 and thus to the valve housing 1. To this end, two parts 15 are secured by means of a snap fit within the bore 11, suitable grooves 16 adapted to receive corresponding projections of parts 15 being provided in the wall of hub 10 defining bore 11.

As shown in the FIGURE, each part 15 includes an inwardly projecting portion 17 that encircles rod 12 with a fairly large radical clearance. The portions 17 are so positioned as to define an annular recess within which is disposed disc 14, appropriate surfaces of projecting portions 17 constituting abutment surfaces for disc 14, which surfaces thus limit the axial movement of valve disc 30 with respect to disc 14 and hence with respect to housing 1.

Two thin-walled, elastic annular diaphragms 18 made of soft rubber and preferably being conically shaped, when in an unstressed condition, to permit easy axial movement extend between the axial extremities of parts 15 and the rod 12. The inner edge of each diaphragm 18, which is connected to rod 12, is reinforced by a rim 19 that fits tightly around the rod 12. The external circumference of each diaphragm 18, which is connected to a respective part 15, is supplied with a sealing rim 20 that is fitted in a recess in part 15, thus wedging the outer edge of the diaphragm 18 between the wall of bore 11 and the associated part 15.

A labyrinth, or damping, chamber 32 is thus defined by the rod 12 with disc 14, the two diaphragms 18 and the parts 15, and this chamber is filled with a mass 21 of a high viscosity fluid, e.g. silicone oil, which flows within the labyrinth chamber 32 when the valve disc 30 moves in relation to the fixed valve rod 12 and disc 14.

With the above-described structure of the valve disc 30 for a spring-loaded PEEP valve, the valve designer or engineer can easily coordinate the flow path of the labyrinth chamber 32 and the viscosity of the confined fluid 21 so that a critical damping is obtained of the vibratory system composed of the prestressed spring 5, the valve disc 30 and the volume of compressed air present, during expiration, between the patient's air passages and the valve disc 30.

When the above-described valve is connected by means of opening 3 to the expiratory outlet of ventilating apparatus, and a patient exhales via the valve, the valve disc 30 will be lifted off its seat 13, thus allowing a through flow of exhaled air to the ambient atmosphere, when the patient exerts an expiratory pressure sufficient to overcome the spring force acting on the downstream side of the valve disc 30. Because the damping chamber 32 inside the valve disc 30 produces a damping action by means of the viscous fluid, no damping force will result when the valve disc 30 remains stationary in relation to the fixed valve rod 12. Only when the valve disc 30 is mobile will a reactive force be set up, resulting from the pressure loss caused by the fluid flowing in the labyrinth chamber 32, and the direction of this force will always be opposed to that of the instantaneous direction of movement of valve disc 30.

Thus, when expiration begins, movement of the valve disc 30 will start at a pressure determined solely by the spring force and the area of the valve disc. During the subsequent opening movement, the spring force plus a contribution from the damping device act against the pressure exerted by the expired air on the valve disc 30. When this opening movement ceases, the spring force and the expiratory pressure toward the valve disc will again solely determine the position of the disc 30 in relation to the valve seat 13.

Should the pressure of the expired air fall as a result of pressure vibrations in the air or decreasing expiratory velocity, the spring force will cause the valve disc 30 to move toward the valve seat 13, whereby the damping device will create a force acting in the direction opposite to the spring force, which in turn will counteract the acceleration of the valve disc 30 towards the seat 13. When the damping device as described is tuned to critical damping, it will not be possible for the valve disc 30 to set up resonance vibrations by these movements, and the opening and closing pressure of the valve will be determined solely by the adjustable spring force setting.

In preferred embodiments of the invention, the two annular diaphragms 18 can each be made of a relatively soft silicone rubber of a type having a shore hardness of the order of about A 30. Such a material has been found to be particularly suitable because of its long service life, i.e. its tendency to age slowly, and its good temperature stability. By making diaphragms 18 slightly conical, as illustrated in the FIGURE, and as mentioned above herein, they will not be tensilely stressed, but will rather experience a slight amount of bowing, during movement of support member 31 between its end positions. The diaphragms 18, which can be given a thickness as small as 0.2 to 0.3 mm, will thus essentially not add any component to the forces influencing the movement of the valve disc 30.

In order to avoid the necessity for providing extremely narrow passages, and thus small tolerances, between the valve rod 12 and disc 14, on the one hand, and the interior surfaces of parts 15, on the other hand, use can advantageously be made, in preferred embodiments of the invention, of a high viscosity silicone grease as the fluid constituting mass 21. One highly suitable example would be a silicone grease having a viscosity corresponding to "penetration", of 350–400, as measured according to ASTM standard D-217. When such a fluid material is employed, a valve rod 12 having a diameter of 3 mm can be employed, and the disc 14 an interior surfaces of parts 15 can be dimensioned to provide a diametral clearance of about 0.5 mm between rod 12 and disc 14, on the one hand, and the interior surfaces of parts 15, including portions 17, on the other hand. Such dimensions, in conjunction with the above-mentioned fluid, will produce substantially critical damping for an embodiment in which valve seat 13 has a diameter of the order of 30 mm, with an adjustment range of zero to 10 cm and an opening pressure H 20, with the total range of the movable parts being of the order of 6 to 7 grams.

It will be understood that the above description of the present invention is susceptible to various modifications, changes and adaptations, and the same are intended to be comprehended within the meaning and range of equivalents of the appended claims.

What is claimed is:

1. In an expiration valve including: a valve housing presenting an inlet arranged to be connected to the expiratory outlet of ventilating apparatus, and an outlet; means defining a valve seat disposed within the housing between its inlet and outlet; a valve disc arranged to cooperate in a sealing manner with the valve seat: a compression spring acting against the side of the valve disc which is remote from the valve seat for biasing the valve disc into its sealing position against the valve seat in the direction counter to the air flow direction between the inlet and the outlet; and means defining a damping chamber disposed within the valve disc and containing a viscous fluid, for causing movement of the viscous fluid within the chamber to damp vibrations of the disc during movement of the disc within said housing, the improvement wherein:

said valve disc is provided with a through bore;

said valve further comprises a valve rod secured within said housing and extending through said valve disc bore between the opposite sides of said valve disc;

said means defining a damping chamber comprises a pair of flexible, annular diaphragms each extending between said valve rod and said valve disc, and spaced apart along the length of said rod to delimit opposite ends of said damping chamber;

said valve further comprises a rigid disc disposed within said damping chamber and fixed to said valve rod; and said valve disc is provided with portions extending radially inwardly toward the interior of its bore to define abutment surfaces for said rigid disc in order to limit the axial movement of said valve disc relative to said valve rod.

2. An arrangement as defined in claim 1 wherein each said diaphragm is of soft rubber and has a conical configuration.

3. An arrangement as defined in claim 1 wherein said viscous fluid is constituted by a silicone oil.

4. An arrangement as defined in claim 1 further comprising a threaded cap secured to said housing in a manner to be adjustable positioned relative thereto, and supporting the end of said compression spring remote from said valve disc.

5. An arrangement as defined in claim 1 or 4 wherein said valve disc comprises a rigid support member and a flexible annular diaphragm arranged to engage said valve seat and having its inner edge secured to said rigid support member.

* * * * *